US012083098B2

(12) United States Patent
Tucker et al.

(10) Patent No.: US 12,083,098 B2
(45) Date of Patent: Sep. 10, 2024

(54) TREATMENT OF IDIOPATHIC PULMONARY FIBROSIS WITH GLYCOGEN SYNTHASE KINASE 3 FORM β INHIBITORS

(71) Applicant: Actuate Therapeutics Inc., Fort Worth, TX (US)

(72) Inventors: Torry A. Tucker, Tyler, TX (US); Steven Idell, Tyler, TX (US)

(73) Assignee: ACTUATE THERAPEUTICS INC., Fort Worth, TX (US)

( * ) Notice: Subject to any disclaimer, the term of this patent is extended or adjusted under 35 U.S.C. 154(b) by 943 days.

(21) Appl. No.: 17/056,238

(22) PCT Filed: May 16, 2019

(86) PCT No.: PCT/US2019/032639
§ 371 (c)(1),
(2) Date: Nov. 17, 2020

(87) PCT Pub. No.: WO2019/222483
PCT Pub. Date: Nov. 21, 2019

(65) Prior Publication Data
US 2021/0212988 A1    Jul. 15, 2021

Related U.S. Application Data

(60) Provisional application No. 62/672,864, filed on May 17, 2018.

(51) Int. Cl.
*A61K 31/407* (2006.01)
*A61K 9/00* (2006.01)
*A61P 11/00* (2006.01)

(52) U.S. Cl.
CPC .......... *A61K 31/407* (2013.01); *A61K 9/0073* (2013.01); *A61P 11/00* (2018.01)

(58) Field of Classification Search
CPC .................................................. A61K 31/407
See application file for complete search history.

(56) References Cited

U.S. PATENT DOCUMENTS

| 8,207,216 | B2 * | 6/2012 | Kozikowski | ............ | A61P 35/00 |
| | | | | | 548/430 |
| 11,136,334 | B2 * | 10/2021 | Zhang | ................ | C07D 491/056 |
| 11,407,759 | B2 * | 8/2022 | Zhang | ..................... | A61P 35/00 |
| 2016/0375006 | A1 | 12/2016 | Scolnick et al. | | |

FOREIGN PATENT DOCUMENTS

| CN | 108 014 340 | A | 5/2018 |
| JP | 2009-508947 | A | 3/2009 |
| JP | 2014-503598 | A | 2/2014 |
| JP | 2015-535233 | A | 12/2015 |
| JP | 2016-60741 | A | 4/2016 |
| JP | 2016-527275 | A | 9/2016 |
| WO | WO 2008/077138 | A1 | 6/2008 |
| WO | 2014/165851 | A1 | 10/2014 |
| WO | 2015/155738 | A2 | 10/2015 |

OTHER PUBLICATIONS

Boren et al., "Inhibition of Glycogen Synthase Kinase 3β Blocks Mesomesenchymal Transition and Attenuates *Streptococcus pneumonia*—Mediated Pleural Injury in Mice", The American Journal of Pathology, vol. 187, No. 11, Nov. 2017, pp. 2461-2472.
Ivanova et al., "Inhalation Treatment of Pulmonary Fibrosis by Liposomal Prostaglandin E2", Eur J. Pharm Biopharm. 84(2), Jun. 2013, 20 pages.
Pal et al., "Inhibition of GSK-3 Induces Differentiation and Impaired Glucose Metabolism in Renal Cancer", Small Molecule Therapeutics, Dec. 2013, pp. 285-296.
Tucker et al., "Myocardin is Involved in Mesothelial-Mesenchymal Transition of Human Pleural Mesothelial Cells", American Journal of Respiratory Cell and Molecular Biology, vol. 61 No. 1, Jul. 2019, 11 pages.
Kamata et al., "KIF5A Transports Collagen Vesicles of Myofibroblasts During Pleural Fibrosis", Scientific Reports, Jul. 2017, 12 pages.
Tucker et al., "Organizing Empyema Induced in Mice by *Steptococcus pneumoniae*: Effects of Plasminogen Activator Inhibitor-1 Deficiency", Clin Trans Med 5:17 (2016) 18 pages.
Sisson et al, "Inhibition of Myocardin-Related Transcription Factor/ Serum Response Factor Signaling Decreases Lung Fibrosis and Promotes Mesenchymal Cell Apoptosis", Am J. Pathol 2015, 185 pp. 969-860.
Mackinnon et al., "Regulation of Transforming Growth Factor-1-driven Lung Fibrosis by Galectin-3", American Journal of Respiratory and Critical Care Medicine, vol. 185, No. 5, (2012), pp. 537-546.
European Patent Application No. 19803888.7; Extended Search Report; dated Mar. 7, 2022; 14 pages.
Baarsma et al.; "Glycogen synthase kinase-3 (GSK-3) regulates TGF-β1-induced differentiation of pulmonary fibroblasts"; British Journal of Pharmacology; vol. 169 Issue 3; Jun. 2013; p. 590-603.
Tucker et al.; "Glycogen Synthase Kinase-3β Inhibition Attenuates the Progression of Pulmonary Fibrosis"; A68. Molecular Determinants of Remodeling in Lung Fibrosis; May 2018; p. 2 of 5.
Jeffers et al.; "Glycogen Synthase Kinase-3β Inhibition with 9-ING-41 Attenuates the Progression of Pulmonary Fibrosis"; Scientific Reports; vol. 9 Article No. 18925; 2019; 13 pages.
Gurrieri, et al., "3-(2,4-dichlorophenyl)-4-(1-methyl-1H-indol-3-yl)-1H-pyrrole-2,5-dione (SB216763), a glycogen synthase kinase-3 inhibitor, displays therapeutic properties in a mouse model of pulmonary inflammation and fibrosis", J Pharmacol Exp Ther, vol. 332(3), pp. 785-794, Mar. 2010.
Liu, et al., "SB216763, a selective small molecule inhibitor of glycogen synthase kinase-3, improves bleomycin-induced pulmonary fibrosis via activating autophagy", Acta Pharmaceutica Sinica B, vol. 3, No. 4, pp. 226-233, 2013.

(Continued)

*Primary Examiner* — Rei Tsang Shiao
(74) *Attorney, Agent, or Firm* — BakerHostetler

(57) ABSTRACT

Pharmaceutical compositions and methods are described which rely upon glycogen synthase kinase 3 (form β; GSK 3 β) inhibitors, most preferably 9-ING-41, to inhibit fibrotic pulmonary remodeling in vivo including proliferation and differentiation of myofibroblasts to fibrotic fibroblasts in several mouse models. Therapeutic targeting of GSK-3β with the clinically useful specific inhibitor, 9-ING-41, mitigates fibrotic pulmonary remodeling in vivo and provides a mode of therapy of human IPF by specific GSK-3β inhibition with 9-ING-41.

8 Claims, 7 Drawing Sheets

(56) References Cited

OTHER PUBLICATIONS

Tucker, et al., "Plasminogen Activator Inhibitor-1 Deficiency Augments Visceral Mesothelial Organization, Intrapleural Coagulation, and Lung Restriction in Mice with Carbon Black/Bleomycin—Induced Pleural Injury", Am J Respir Cell Mol Biol., vol. 50(2), pp. 316-327, Feb. 2014.
Karmali, et al., "GSK-3β inhibitor, 9-ING-41, reduces cell viability and halts proliferation of B-cell lymphoma cell lines as a single agent and in combination with novel agents", Oncotarget, vol. 8, No. 70, pp. 114924-114934, 2017.
Ougokov, et al., "Inhibition of glycogen synthase kinase-3 activity leads to epigenetic silencing of nuclear factor kappaB target genes and induction of apoptosis in chronic lymphocytic leukemia B cells", Blood, vol. 110, No. 2, pp. 735-742, 2007.
Parameswaran, et al., "Repression of GSK3 restores NK cell cytotoxicity in AML patients", Nat Communications, vol. 7, 11154, 2016.
Ricciardi, et al., "Targeting the Akt, GSK-3, Bcl-2 axis in acute myeloid leukemia", Advances in Biological Regulation, vol. 65, pp. 36-58, 2017.

\* cited by examiner

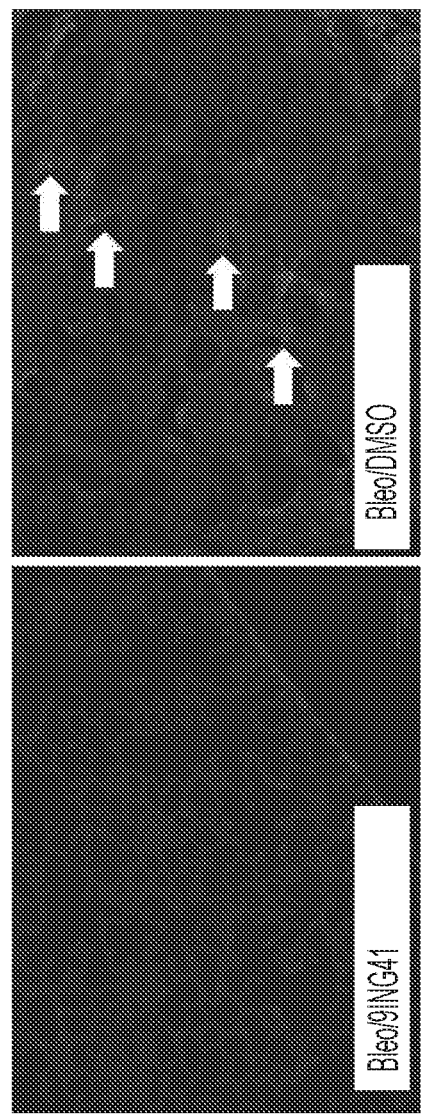

TREATMENT OF IDIOPATHIC PULMONARY FIBROSIS WITH GLYCOGEN SYNTHASE KINASE 3 FORM β INHIBITORS

CROSS-REFERENCE TO RELATED APPLICATIONS

This application is the United States National Stage Application of International Patent Application No. PCT/US2019/032639, filed May 16, 2019 which claims the benefit of priority to U.S. Provisional Application No. 62/672,864, filed on May 17, 2018. The entirety of each of the aforementioned applications is incorporated by reference herein.

GOVERNMENT INTEREST

This invention was made with government support (NIH HL130133) awarded by the National Institutes of Health. The U.S. government has certain rights in the invention.

BACKGROUND OF THE INVENTION

Field of the Invention

The present invention in the field of biochemistry and medicine is directed to methods and composition for using a glycogen synthase kinase 3, form β (GSK-3β) inhibitor, most preferably 9-ING-41, to inhibit fibrotic pulmonary remodeling in vivo and thereby treat idiopathic pulmonary fibrosis (IPF).

Background

Idiopathic pulmonary fibrosis (IPF) is a poorly understood progressive and fatal lung disease for which few, if any, treatments exist other than lung transplantation. Currently available treatments for pulmonary fibrosis are not known to be curative and only slow the progression of the disease. Median survival time (MST) is 3 years after diagnosis (and median survival 5 years after diagnosis is less than 20%). Most forms of interstitial lung diseases and other forms of pulmonary fibrosis are characterized by fibrotic lesions, progressive distortion of alveolar architecture occurs and replacement with fibrotic or scar tissues with excess extracellular matrix (ECM) deposition, resulting in progressive dyspnea and loss of lung function.

GSK-3β is a serine/threonine kinase and is in one of two GSK-3 isoforms (α and β). GSK-3β can regulate the function of a diverse list of targets including transcription factors. GSK-3β also regulates a number of signaling pathways that consequently affect the transcriptional activity of numerous inflammatory mediators.

Because current treatments only slow the progression of the disease, identification of new more, efficacious targets is needed, as are better treatment modalities that might significantly reverse, or reduce mortality from and cure IPF.

SUMMARY OF THE INVENTION

The disclosure is directed to treatment of both pleural and pulmonary fibrosis. In preferred embodiments, these methods are achieved via administration of 9-ING-41, which is well tolerated even at high doses. It also limits scar formation in a mouse model of pleural fibrosis and, as described herein, pulmonary fibrosis. There are no effective therapies for the treatment of scarring and tissue reorganization associated with pleural fibrosis, and existing approaches available for pulmonary fibrosis merely slow its progression but are not curative. 9-ING-41, mitigates fibrotic pulmonary remodeling in vivo, addresses the urgent need for effective therapy of pulmonary fibrosis.

There is currently no effective treatment to reverse lung fibrosis. The present invention addresses this important gap and provides novel compounds and methods for targeting fibrotic lung ("FL") fibroblasts (or myofibroblast)) to effectively treat IPF.

The present invention is directed to a method to inhibit mesomesenchymal transition (MesoMT) of residential pleural mesothelial cells (PMCs) which contributes to expansion of myofibroblasts in the progression to IPF.

The present invention is directed to method of treating idiopathic pulmonary fibrosis (IPF) in a mammalian subject by administering to a mammalian subject in need thereof, an effective amount of a compound of Formula I

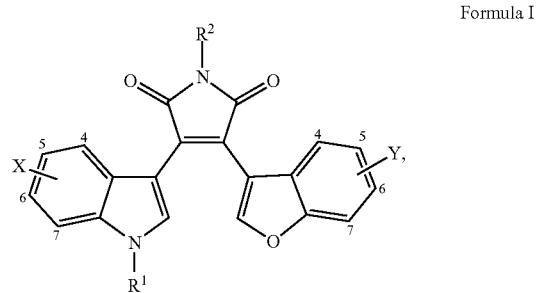

Formula I or a pharmaceutically acceptable salt or solvate thereof, wherein:
X is independently —H, halo, 5,6-methylenedioxy, —CN, —OMe, —OH, —OBn, —CF$_3$, —CH$_2$OH, —CH2OMe, —CH$_2$CH$_2$CO$_2$H, or —CH$_2$CH$_2$CO$_2$Et;
R$^1$ is —H, lower alkyl, lower alkyl substituted with a hydroxy, or lower alkyl substituted with —NH$_2$;
R$^2$ is —H, lower alkyl, lower alkyl substituted with a hydroxy, or lower alkyl substituted with —NH$_2$;
Y is independently —H, halo, —OMe, —OH, —OBn, —CF$_3$, —CH$_2$OH, —CH$_2$OMe, —NO$_2$, —CN, or —C=CH$_2$.

The present invention is also directed to methods of treating IPF in a mammalian subject by administering to a mammalian subject in need thereof, a pharmaceutical composition comprising i) an effective amount of a compound of Formula I or a pharmaceutically acceptable salt or solvate thereof, and ii) a pharmaceutically acceptable carrier or excipient.

The present invention is also directed to a method for treating a mammalian subject having or developing a disease or condition characterized by pulmonary fibrosis, most preferably, IPF in humans, comprising administering to the subject an effective amount of a pharmaceutical composition as above. The compound or composition preferably comprises 9-ING-41 or an analogue thereof that has at least 20% of the biological or biochemical activity of 9-ING-41 in as in vitro or in vivo assay. The most preferable compound is 9-ING-41.

In preferred embodiments of the methods of treating IPF in a mammalian subject, the compound of Formula I is 9-ING-41 or a pharmaceutically acceptable salt or solvate thereof.

In preferred embodiments of the methods of treating PF in a mammalian subject, the mammalian subject is a human.

In preferred embodiments of the methods of treating IPF in a mammalian subject, the administering is by inhalation.

Also provided is a method for inhibiting proliferation and/or differentiation of lung myofibroblasts to fibrotic lung (FL) fibroblasts and reducing proliferation of the FL fibroblasts, comprising contacting the myofibroblasts and FL fibroblasts in a mammalian subject in need thereof, with an antifibrotically effective amount of a compound of Formula I, or a pharmaceutical composition comprising an effective amount of a compound of Formula I or a pharmaceutically acceptable salt thereof, and a pharmaceutically acceptable excipient or carrier.

In preferred embodiments of methods for inhibiting proliferation and/or differentiation of lung myofibroblasts to FL fibroblasts and reducing proliferation of the FL fibroblasts, the compound or Formula I is preferably 9-ING-41 or a pharmaceutically acceptable salt or solvate thereof.

In preferred embodiments of the methods for inhibiting proliferation and/or differentiation of lung myofibroblasts to FL fibroblasts and reducing proliferation of the FL fibroblasts, the mammalian subject is a human.

In preferred embodiments of the methods for inhibiting proliferation and/or differentiation of lung myofibroblasts to FL fibroblasts and reducing proliferation of the FL fibroblasts, the contacting is by inhalation.

The present invention also provides a pharmaceutical composition comprising: (i) an antifibrotically effective amount of a compound of Formula I or a pharmaceutically acceptable salt or solvate thereof, and (ii) a pharmaceutically acceptable carrier or excipient.

In preferred embodiments, Formula I in the pharmaceutical compositions of the invention is 9-ING-41.

In preferred embodiments, the pharmaceutical compositions of the invention are formulated for administration by inhalation.

In another embodiment, the invention is directed to the use of the above compositions for treating IPF in a mammalian subject, wherein an effective amount of said composition is administered to a mammalian subject with IPF.

In preferred embodiments, the composition inhibits GSK-3β, and inhibits proliferation and/or differentiation of lung myofibroblasts to FL fibroblasts, and reduces proliferation of said FL fibroblasts.

In preferred embodiments, the composition comprises an effective amount of 9-ING-41 or a pharmaceutically acceptable salt or solvate thereof.

In preferred embodiments, the mammalian subject is a human.

In preferred embodiments, the composition is administered by inhalation.

Another embodiment is directed to use of a composition as above for the manufacture of a medicament for treatment of IPF in a mammalian subject, preferably a human, in need thereof.

In preferred embodiments, the composition inhibits GSK-3β activity, and inhibits proliferation and/or differentiation of lung myofibroblasts to FL fibroblasts, and reduces proliferation of said FL fibroblasts.

In this use, the compound is preferably 9-ING-41 or a pharmaceutically acceptable salt or solvate thereof. In the above use, the manufacture of the medicament is for administration by inhalation to a human for treatment of IPF.

BRIEF DESCRIPTION OF THE DRAWINGS

FIGS. 2A-2B show lung tissue sections (5 μm) from DMSO vehicle (FIG. 2B) and 9-ING-41 treated (FIG. 2A) mice. Sections were immunostained to visualize collagen deposition (shown as gray) by confocal microscopy. Solid arrows indicate areas of increased collagen-1 deposition. Images are representative of 30 fields/slide/condition. n=6 mice.

DESCRIPTION OF THE PREFERRED EMBODIMENTS

9-ING-41 as a GSK-3β Inhibitor

Figures 1A, 1B:
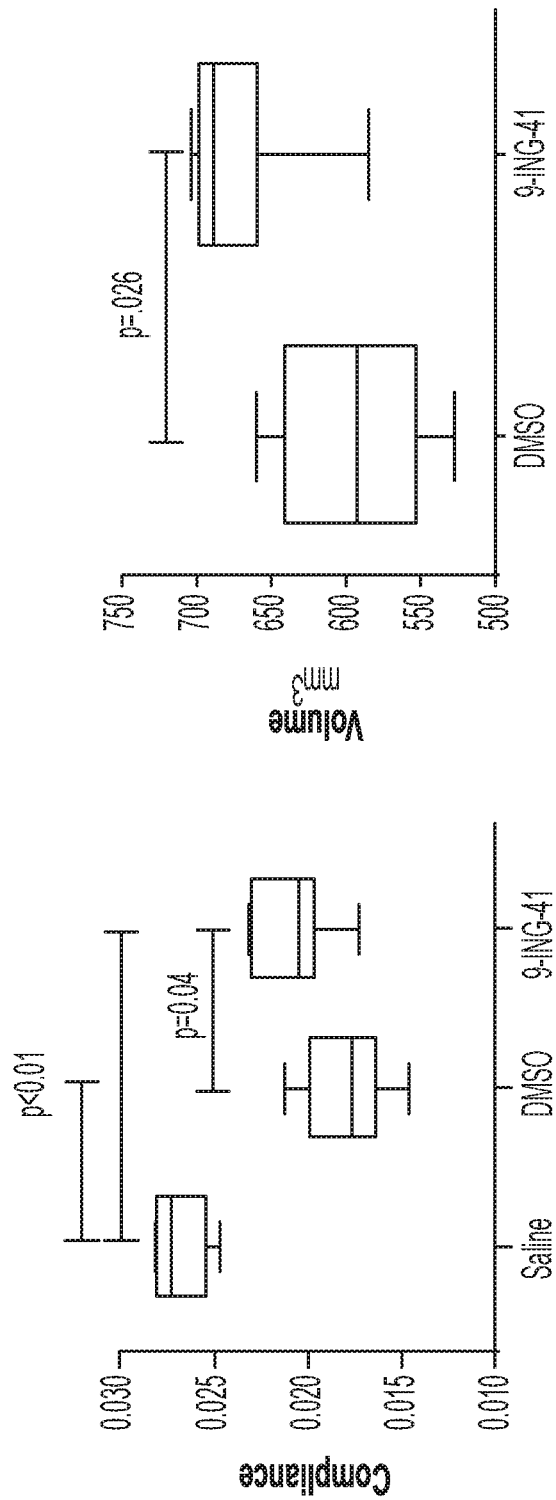
FIGS. 1A-1B are graphs that show that GSK-3β inhibition with 9-ING-41 attenuated pulmonary fibrosis. C57Bl/6J mice were intratracheally administered bleomycin sulfate (0.8 U/kg). After 14 d, mice were either treated with DMSO (vehicle) or the GSK-3β inhibitor, 9-ING-41 (30 mg/kg) by dialing intraperitoneal injection for the following 14 d. At the completion of the 28 d time-course lung compliance (FIG. 1A) was determined using the Scireq flexivent. Lung renditions were also collected by gated CT scan and used to determine lung volumes (FIG. 1).

Compounds useful in the method of the present invention include 9-ING-41, described in U.S. Pat. No. 8,207,216 (Kozikowski et al.), incorporated by reference in its entirety.

Also useful in the present invention are a broader genus of benzofuran-3-yl-(indol-3-yl) maleimide family that share the property of GSK-3β inhibition. Such compounds are encompassed by the Formula I

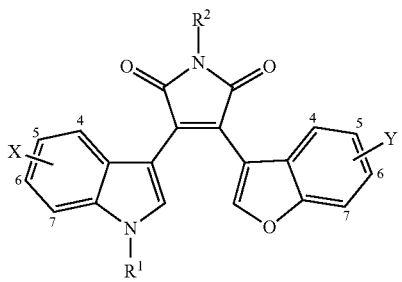

Formula I wherein:
X is independently —H, halo, 5,6-methylenedioxy, —CN, —OMe, —OH, —OBn, —CF$_3$, —CH$_2$OH, —CH2OMe, —CH$_2$CH$_2$CO$_2$H, or —CH$_2$CH$_2$CO$_2$Et;
R$^1$ is —H, lower alkyl, lower alkyl substituted with a hydroxy, or lower alkyl substituted with —NH$_2$;
R$^2$ is —H, lower alkyl, lower alkyl substituted with a hydroxy, or lower alkyl substituted with —NH$_2$;
Y is independently —H, halo, —OMe, —OH, —OBn, —CF$_3$, —CH$_2$OH, —CH$_2$OMe, —NO$_2$, —CN, or —C=CH$_2$.

In compounds of Formula I, X is independently —H, halo, 5,6-methylenedioxy, —CN, —OMe, —OH, —OBn, —CF$_3$, —CH$_2$OH, —CH2OMe, —CH$_2$CH$_2$CO$_2$H, or —CH$_2$CH$_2$CO$_2$Et. Substituent X may be present, independently, at one or more of the positions 4, 5, 6, or 7 of the indole ring in Formula I.

In some embodiments, X is H.
In other embodiments, X is halo (i.e., —F, —Cl, —Br, —I). In some embodiments, X is 5-F.
In other embodiments, X is 5-Br. In other embodiments, X is 5-I.
In other embodiments, X is 5-F, 6-Cl. In other embodiments, X is 5,7-dibromo.
In some embodiments, X is 5,6-methylenedioxy.
In some embodiments, X is —CN.
In some embodiments, X is —OMe (i.e., —O—CH$_3$) In some embodiments, X is —OH.
In some embodiments, X is —OBn (i.e., —O-benzyl).
In some embodiments, X is —CF$_3$ In some embodiments, X is —CH$_2$OH.
In some embodiments, X is —CH$_2$OMe.
In some embodiments, X is —CH$_2$CH$_2$CO$_2$H.
In some embodiments, X is —CH$_2$CH$_2$CO$_2$Et.
In compounds of Formula I, R$^1$ is H, lower alkyl, lower alkyl substituted with a hydroxy, or lower alkyl substituted with —NH$_2$.
In some embodiments, R$^1$ is H.
In other embodiments, R$^1$ is lower alkyl. As used herein, lower alkyl refers to a saturated, straight chain or branched hydrocarbon group. Examples of lower alkyl groups include methyl, ethyl, propyl, isopropyl, and the like. In some embodiments, R$^1$ is —CH$_3$ (i.e., methyl).
In other embodiments, R$^1$ is lower alkyl substituted with a hydroxy.
In other embodiments, R$^1$ is lower alkyl substituted with —NH$_2$.
In compounds of Formula I, R$^2$ is —H, lower alkyl, lower alkyl substituted with a hydroxy, or lower alkyl substituted with —NH$_2$.
In some embodiments, R$^2$ is H.
In other embodiments, R$^2$ is lower alkyl. In some embodiments, R$^2$ is —CH$_3$ (i.e., methyl).
In other embodiments, R$^2$ is lower alkyl substituted with a hydroxy.
In other embodiments, R$^2$ is lower alkyl substituted with —NH$_2$.

In compounds of Formula I, Y is independently —H, halo, —OMe, —OH, —OBn, —CF$_3$, —CH$_2$OH, —CH$_2$OMe, —NO$_2$, —CN, or —C=CH$_2$. Substituent Y may be present, independently, at one or more of the positions 4, 5, 6, or 7 of the benzofuran ring in Formula I.

In some embodiments, Y is H.
In other embodiments, Y is halo (i.e., —F, —Cl, —Br, —I). In some embodiments, Y is 5-F.
In other embodiments, Y is 5-Br. In other embodiments, Y is 5-I.
In some embodiments, Y is —CN.
In some embodiments, Y is —OMe (i.e., —O—CH$_3$). In some embodiments, Y is 7-OCH$_3$.
In some embodiments, Y is —OH.
In some embodiments, Y is —OBn (i.e., —O-benzyl).
In some embodiments, Y is —CF$_3$.
In some embodiments, Y is —CH$_2$OH. In some embodiments, Y is 6-CH$_2$OH.
In some embodiments, Y is —CH$_2$OMe.
In some embodiments, Y is —C=CH$_2$.
In some embodiments, Y is —NO$_2$.
In some embodiments of the compounds of Formula I,
X is preferably 5,6-methylenedioxy (the substituent in 9-ING-41),
In some embodiments, R$^1$ is selected from the group consisting of H, lower alkyl, lower alkyl substituted with a hydroxy, lower alkyl substituted with —NH$_2$, and is preferably methyl; In some embodiments, R$^2$ is selected from the group consisting of H, lower alkyl, lower alkyl substituted with a hydroxy, lower alkyl substituted with —NH$_2$, and is preferably H;
In some embodiments, Y is selected from the group consisting of a 5- or 6-halo group, a 5- or 6-NO$_2$, —CN, and —C=CH$_2$, group; Y is preferably 5-fluorine (5-F).
In some embodiments of the compound of Formula I, X is 5,6-methylenedioxy; R$^1$ is —CH$_3$; R$^2$ is H, and Y is 5-F. This embodiment is 9-ING-41, which has the structure shown in Formula II below.

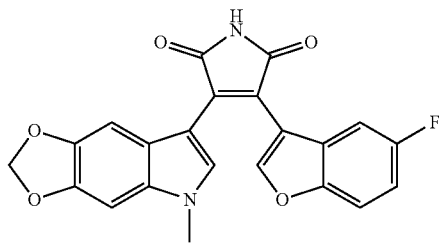

Formula II

The above compounds with different substituents in Formula I than 9-ING-41 are considered analogues thereof.
General methods of synthesizing compounds of Formula I are known in the art, some of which is described in the '216 patent, supra.

In Vitro Testing of Compositions
The compounds of this invention are tested for their biological activity, e.g., anti-fibrotic activity, their ability to inhibit the enzyme GSK-3β, and/or inhibit proliferating and collagen-producing fibroblasts/myofibroblasts, or of fibrotic lung fibroblasts using any one of the methods or assays described and/or exemplified herein or others that are well-known in the art.

In Vivo Testing of Compositions

The ability of a compound to inhibit pulmonary fibrosis in an animal, preferably a mouse, treated with BLM- or constitutively active TGF-β adenoviral vectors (see Example VI), is a preferred test for assessing the functional/pharmaceutical activity of the compound. Other tests known in the art that measure the same type of activity may also be used.

Method of Preventing or Treating Lung Injury and Fibrosis

The compounds and compositions described herein are used in methods to inhibit the enzyme GSK-3β, to inhibit proliferation of collagen-producing fibroblasts/myofibroblasts vitro or in vivo, and to treat pulmonary fibrosis/IPF.

Pharmaceutical and Therapeutic Compositions and their Administration

The compounds that may be employed in the pharmaceutical compositions of the invention include the compounds described above, preferably 9-ING-41, as well as analogues thereof and pharmaceutically acceptable salts or solvates of these compounds. "Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like.

Sample base-addition salts include those derived from ammonium, potassium, sodium and, quaternary ammonium hydroxides, such as for example, tetramethylammonium hydroxide. Chemical modification of a pharmaceutical compound (i.e., drug) into a salt is a technique well known to pharmaceutical chemists for obtaining improved physical and chemical stability, hygroscopicity, flowability and solubility of compounds. See, e.g., H. Ansel et al., *Pharmaceutical Dosage Forms and Drug Delivery Systems* ($6^{th}$ Ed. 1995), e.g., at pp. 196 and 1456-1457.

As stated above, the compounds of the invention possess the ability to inhibit the enzyme GSK-3β and are exploited in the treatment of pulmonary fibrosis.

The compounds of the invention, as well as the pharmaceutically acceptable salts or solvates thereof, may be incorporated into convenient dosage forms, such as capsules, impregnated wafers, tablets or preferably, injectable preparations. Solid or liquid pharmaceutically acceptable carriers may be employed. "Pharmaceutically acceptable," such as pharmaceutically acceptable carrier, excipient, etc., means pharmacologically acceptable and substantially non-toxic to the subject to which the particular compound is administered.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Gennaro, AR, *Remington: The Science and Practice of Pharmacy*, Lippincott Williams & Wilkins Publishers; $21^{st}$ Ed, 2005 (or latest edition).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, most preferably humans.

The compositions of the present invention may be administered to the subject by any suitable route of administration, including orally, perorally, by inhalation, subcutaneously, intramuscularly, intravenously, transdermally, vaginally, rectally, or in any combination thereof.

In some embodiments, the compositions of the present invention are administered orally, perorally, by inhalation, subcutaneously, intramuscularly, or intravenously.

In some embodiments, the compositions of the present invention are administered orally.

In other embodiments, the compositions of the present invention are administered perorally.

In other embodiments, the compositions of the present invention are administered by inhalation.

In other embodiments, the compositions of the present invention are administered subcutaneously.

In other embodiments, the compositions of the present invention are administered intramuscularly.

In other embodiments, the compositions of the present invention are administered intravenously.

The term "systemic administration" refers to administration of the therapeutic compound in a manner that results in the introduction of the compound into the subject's circulatory system or otherwise permits its spread throughout the body, such as intravenous (i.v.) injection or infusion. "Regional" administration refers to administration into a specific, and somewhat more limited, anatomical space, such as instillation or inhalation into the lung, the preferred route, or intrapleural, intraperitoneal, intrathecal, subdural, or to a specific organ. Other examples include intranasal, which is one route that corresponds to instillation or inhalation into the lungs, intrabronchial, intra-aural or intraocular, etc. The term "local administration" refers to administration of a composition or drug into a limited, or circumscribed, anatomic space, such as subcutaneous (s.c.) injections, intramuscular (i.m.) injections. One of skill in the art would understand that local administration or regional administration often also result in entry of a composition into the circulatory system, so that s.c. or i.m. are also routes for systemic administration. Instillable, injectable or infusible preparations can be prepared in conventional forms, either as solutions or suspensions, solid forms suitable for solution or suspension in liquid prior to injection or infusion, or as emulsions. Though the preferred regional routes of administration are into the lungs, the pharmaceutical composition may be administered systemically or topically or transdermally either separately from, or concurrently with, instillation or inhalation into the lungs.

Other pharmaceutically acceptable carriers for compositions of the present invention are liposomes, pharmaceutical compositions in which the active polypeptide is contained either dispersed or variously present in corpuscles consisting of aqueous concentric layers adherent to lipidic layers. The active compound is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

Therapeutic Methods

The methods of this invention may be used to treat pulmonary fibrosis also referred to as IPF in a subject in need thereof. The term "treating" is defined broadly to include, at least the following: inhibiting, reducing, ameliorating, preventing, reducing the occurrence or recurrence, including the frequency and/or time to recurrence or the severity of symptoms of the disease or condition being treated or prevented. This may occur as a result of inhibiting epithelial cell death, inhibiting fibroblast proliferation, any of the other biological or biochemical mechanisms disclosed herein as being associated with, or responsible for, IPF.

The benzofuran-3-yl-(indol-3-yl) maleimide GSK-3β inhibitors (i.e., the compounds of Formula I), most preferably, 9-ING-41 or pharmaceutically acceptable salt or solvate thereof, is preferably administered as a pharmaceutical composition as described above.

Doses of the compound preferably include pharmaceutical dosage units comprising an effective amount of 9-ING-41. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By "an effective amount" is meant an amount sufficient to achieve a regional concentration or a steady state concentration in vivo which results in a measurable reduction in any relevant parameter of disease.

By "antifibrotically effective amount" is meant an amount sufficient to inhibit or reduce proliferation and/or differentiation of lung myofibroblasts to fibrotic lung (FL) fibroblasts, or to and reducing proliferation of the FL fibroblasts.

The amount of active compound to be administered depends on which compound (e.g., 9-ING-41) is selected, the precise disease or condition, the route of administration, the health and weight of the recipient, the existence of other concurrent treatment, if any, the frequency of treatment, the nature of the effect desired, and the judgment of the skilled practitioner.

A preferred single dose, given once daily for treating a subject, preferably a mammal, more preferably human who is suffering from or susceptible to IPF resulting therefrom is between about 0.2 mg/kg and about 250 mg/kg, (for example, 0.2, 0.4, 0.6, 0.8, 1, 1.5, 2, 2.5, 3, 3.5, 4, 4.5, 5, 5.5, 6, 6.5, 7, 7.5, 8, 8.5, 9, 9.5, 10, 12, 14, 16, 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, or 250 mg/kg of active compound), between about 0.2 mg/kg and about 10 mg/kg; between about 0.5 mg/kg and about 5 mg/kg; between about 1 mg/kg and about 3 mg/kg, or preferably between about 10 mg/kg and about 50 mg/kg, for example, via inhalation. Such a dose can be administered daily for anywhere from about 3 days to one or more weeks. Chronic administration is also possible, though the dose may need to be adjusted downward as is well-understood in the art. The foregoing ranges are, however, suggestive, as the number of variables in an individual treatment regimen is large, and considerable excursions from these preferred values are expected.

For continuous administration, e.g., by a pump system such as an osmotic pump that was used in some of the experiments described below, a total dosage for a time course of about 1-2 weeks is preferably in the range of 1 mg/kg to 1 g/kg (e.g., 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg/kg) preferably 20-300 mg/kg, more preferably 50-200 mg/kg. After such a continuous dosing regimen, the total concentration of the active compound is preferably in the range of about 0.5 to about 50 µM (e.g., 0.5, 1, 5, 10, 15, 20, 25, 30, 35, 40, 45, 50 µM), preferably about 1 to about 10 µM.

An effective concentration of the active compound for inhibiting GSK-3β or preventing myofibroblast and fibrotic lung fibroblast proliferation in vitro is in the range of about 0.5 µM to about 100 µM (e.g., 0.5, 1, 5, 10, 15, 20, 25, 30, 35, 40, 45, 50, 55, 60, 65, 70, 75, 80, 85, 90, 95, 100 µM), more preferably from about 2 µM to about 20 µM. Effective concentrations, doses and optimal dose ranges may be determined in vitro using the methods described herein.

In the methods of the present invention, the compounds or compositions may be administered to the subject by any suitable route of administration, including orally, perorally, by inhalation, subcutaneously, intramuscularly, intravenously, transdermally, vaginally, rectally, or in any combination thereof.

In some embodiments, the compounds or compositions are administered orally, perorally, by inhalation, subcutaneously, intramuscularly, or intravenously.

In some embodiments, the compounds or compositions are administered orally.

In other embodiments, the compounds or compositions are administered perorally.

In other embodiments, the compounds or compositions are administered by inhalation.

In other embodiments, the compounds or compositions are administered subcutaneously.

In other embodiments, the compounds or compositions are administered intramuscularly.

In other embodiments, the compounds or compositions are administered intravenously.

Having now generally described the invention, the same will be more readily understood through reference to the following examples which are provided by way of illustration, and are not intended to be limiting of the present invention, unless specified. The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Materials and Methods and Two Pulmonary Fibrosis Models

All animal studies were approved by the Institutional Animal Care and Use Committee at the University of Texas Health Science Center at Tyler. C57BL/6 mice (10-12 weeks of age, ≈20 g (from Jackson Laboratory, Bar Harbor ME) were first anesthetized with xylazine/ketamine by intraperitoneal (TP) injection. Lung injury was then initiated in accordance with (Sisson T H et al., *Am J Pathol* 2015, 185:969-860) with some modifications. Bleomycin sulfate (Teva, 0.8 units/kg) was administered intratracheally via an intratracheal cannula. Animals were monitored daily for sign of respiratory distress, significant weight loss or moribund condition. The control group received normal saline under the same conditions.

Treatments were begun 14 d after the initiation of injury. For GSK-3β inhibitor studies, treatment with 9-ING-41 (gift from Actuate Therapeutics, Ft. Worth, TX), at 30 mg/kg, or vehicle control dimethylsulfoxide/DMSO in a volume of 40 μl, was administered daily by IP injection for up to 14 d.

At the completion of the 28 d time course mice were evaluated by flexivent (Tucker T et al., *Am J Respir Cell Mol Biol* 2019 (doi: 10.1165/rcmb.2018-0121OC. Epub ahead of print); Kamata H et al., *Sci Rep* 2017, 7:4556; Boren J et al., supra; Tucker T A et al., 2014, supra; Tucker T A et al., *Clin Transl Med* 5: 17, 2016) for changes in pulmonary function including elastance and compliance. Briefly, mice were anesthetized with a ketamine/xylazine mixture. Anesthetized mice were intubated by inserting a sterile, 20-gauge intravenous cannula through the vocal cords into the trachea and were maintained under anesthesia using isoflurane during pulmonary function testing. Measurements were performed using the flexiVent system (SCIREQ, Tempe AZ). The "snapshot perturbation method" was used to determine lung compliance, according to manufacturer's specifications. At 28 d, mice were euthanized and lungs harvested en bloc. Lung morphometry was determined by trichrome staining of 5 μm lung tissue sections as described in the above cited references. All tissue sections were first deparaffinized and subjected to antigen retrieval using a citrate buffer at 95° C. for 20 minutes. Tissue analyses, collagen deposition and localization were initially assessed by Trichrome staining. Immunofluorescence was used to visualize α-SMA (MAB1420, R&D), Confocal microscopy was then used to visualize immunofluorescence and co-localization of the markers. Images were acquired from a field of view at 0.4-μm z-axis increments with the LSM 510 Meta confocal system (Carl Zeiss) at 40× as described.

In a second model, pulmonary fibrosis was initiated by intratracheal instillation of constitutively active TGF-β adenoviral vectors (Ad-TGF-β) bearing C223S/C225S mutations, as reported by Mackinnon A C et al., *Am J Respir Crit Care Med* 2012, 185:537-46) with some modifications. Briefly, $3 \times 10^8$ pfu of Ad-TGF-β or eGFP adenovirus control vector (Ad-eGFP) were administered intratracheally in a volume of 40 μl. Mice were then monitored daily until the completion of the 14 d time-course. For GSK-3β inhibition studies, mice received daily 9-ING-41 treatment 7 d after administration of the adenoviral vectors. At the conclusion of the time-course pulmonary function testing and CT scans were performed as described (Tucker T et al., 2019, supra; Kamata H et al., 2017, supra; Boren J et al., 2017, supra; Tucker T A et al., 2016, supra.

All statistical analyses of animal studies was performed using the Mann Whitney U test. (Student's t-test was used for in vitro studies). A p-value of less than 0.05 was considered significant.

Example II

9-ING-41 Improves Bleomycin Mediated Decrements of Lung Function and Volume.

As shown in FIGS. 1A-1B, GSK-3β inhibition with 9-ING-41 attenuated pulmonary fibrosis. C57Bl/6J mice intratracheally administered bleomycin sulfate (0.8 U/kg) and after 14 d, were either treated with DMSO (vehicle) or the GSK-3β inhibitor, 9-ING-41 (30 mg/kg). Drugs were delivered via intraperitoneal (ip) injection in a volume of 40 μl for up to 14 d. At the completion of the 28 d course, lung compliance was determined using the Scireq flexivent. Lung renditions were also collected by gated CT scan. These renditions were then used to determine lung volumes. 9-ING-41 treatment significantly improved decrements of lung compliance (p=0.04) and volume (p=0.026).

Example III

9-ING-41 Treatment Blocks Collagen Deposition in Bleomycin-Induced Pulmonary Fibrosis: Trichrome Lung tissue sections (5 μm) were prepared from vehicle and 9-ING-41-treated. The sections were deparaffinized and Trichrome stained to detect changes in lung architecture and collagen deposition (Trichrome images not shown). Images were taken at 20× and represent 30 fields/slide/mouse, n=6 animals per treatment.

Fibrotic foci consistent with bleomycin-induced pulmonary fibrosis were found throughout the injured lung. Areas of matrix deposition were readily and uniformly present throughout the lung. 9-ING-41 treated mice also demonstrated areas of injury; however, these areas were fewer in number and smaller compared to those found in the vehicle treated animals. Further, collagen deposition within the fibrotic lesions was generally reduced in 9-ING-41-treated mice (FIG. 2A) compared to DMSO-treated controls (FIG. 2B). See, also, FIGS. 5A-5F.

Example IV

Figure 6A:
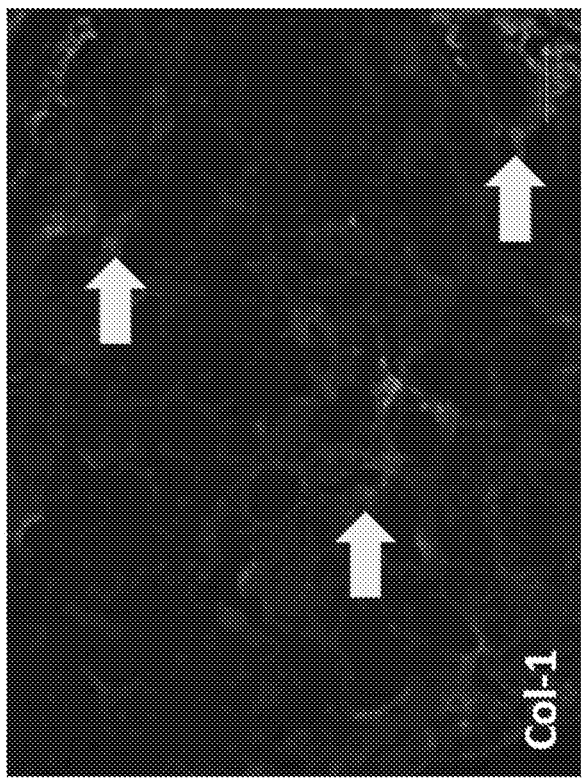
FIGS. 6A-6B show lung sections from vehicle (FIG. 6B) and 9-ING-41-treated (FIG. 6A) mice immunostained for collagen 1 (Col-1) deposition and imaged by confocal microscopy at 40×. Solid arrows indicate areas of collagen deposition within the injured lung. These data show that GSK-3β inhibition with 9ING41 reduced collagen deposition in fibrosing lung injury.
Figure 6B:
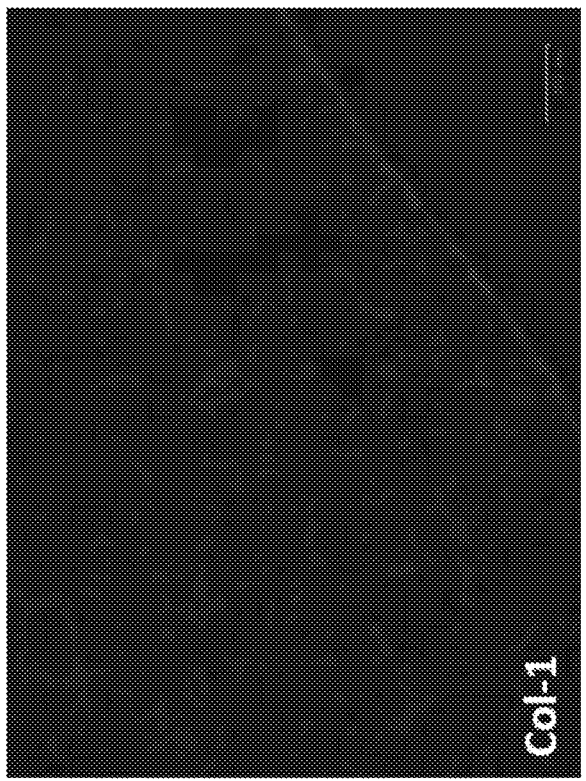

9-ING-41 Treatment Blocks Collagen Deposition in Pulmonary Fibrosis: Collagen Imaging Lung sections from vehicle and 9-ING-41-treated mice were immunostained for α-SMA, a marker of myofibroblast differentiation. Images (FIGS. 6A and 6B) were taken by confocal microscopy at 40×. 9-ING-41 treatment reduced α-SMA expression in 9-ING-41 treated mice when compared to vehicle treated controls (DMSO). Solid arrows indicate areas of collagen α-SMA expression. Images were representative of 30 fields/mouse and n=3 mice/treatment.

Lung sections from vehicle and 9-ING-41-treated mice were immunostained for collagen 1 deposition and imaged by confocal microscopy at 40×. 9-ING-41 reduced collagen 1 deposition in bleomycin injured lungs were compared to vehicle (DMSO) treated controls. These results showed that GSK-3β inhibition with 9-ING-41 reduced collagen deposition in fibrosing lung injury.

Example V

9-ING-41 Appears to Reduce Markers of MesoMT: α-SMA

Figure 7B:
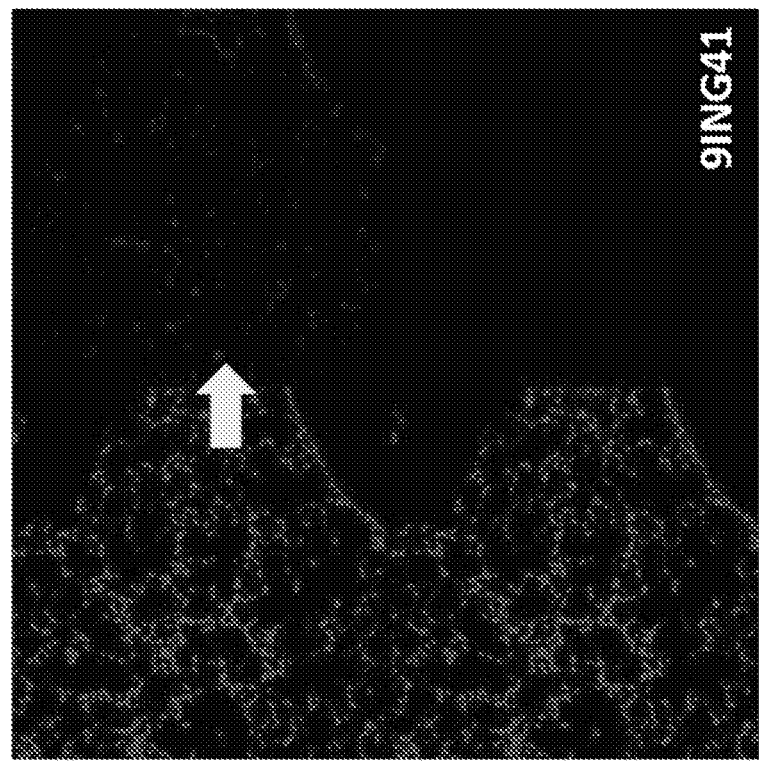
FIGS. 7A-7B show lung sections from vehicle (FIG. 7B) and 9-ING-41-treated (FIG. 7A) mice immunostained for α-SMA, a marker of myofibroblast differentiation. Images were taken by confocal microscopy at 40×. Solid arrows indicate areas of collagen α-SMA expression. Images are representative of 30 fields/mouse and n=3 mice/treatment.
Figure 7A:
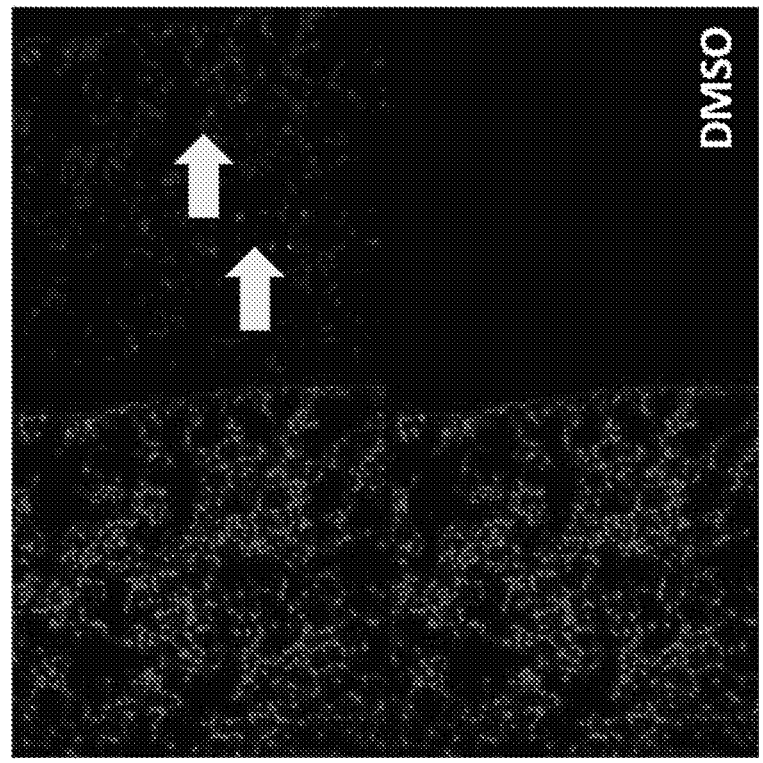

Lung sections from vehicle and 9-ING-41-treated mice were immunostained for α-SMA, a marker of myofibroblast differentiation. Images (FIGS. 7A and 7B) were taken by confocal microscopy at 40×. Solid arrows indicate areas of collagen α-SMA expression. Images are representative of 30 fields/mouse and n=3 mice/treatment. 9-ING-41 treatment reduced α-SMA expression in drug treated mice when compared to vehicle treated controls.

Example VI

9-ING-41 Improves TGF-β-Adenovirus-Induced Lung Damage

Pulmonary fibrosis was initiated by intratracheal instillation of constitutively active TGF-β adenoviral vectors (Ad-TGF-0) bearing C223S/C225S mutations, as previously reported (Mackinnon A C et al., *Am J Respir Crit Care Med* 2012, 185:537-46) with some modifications. Briefly, 3×10$^8$ plaque forming units (pfu) of Ad-TGF-β or eGFP adenovirus control vector (Ad-eGFP) were administered intratracheally in a volume of 40 μl. Mice were then monitored daily until the completion of the 14 d time-course. For GSK-3β inhibition studies, mice received daily 9-ING-41 treatment 7 d after administration of the adenoviral vectors. At the conclusion of the time-course pulmonary function testing and CT scans were performed as described (Tucker T et al., 2019, supra; Kamata H et al., 2017, supra; Boren J et al., 2017, supra; Tucker T A et al., 2016, supra.

Figure 3:
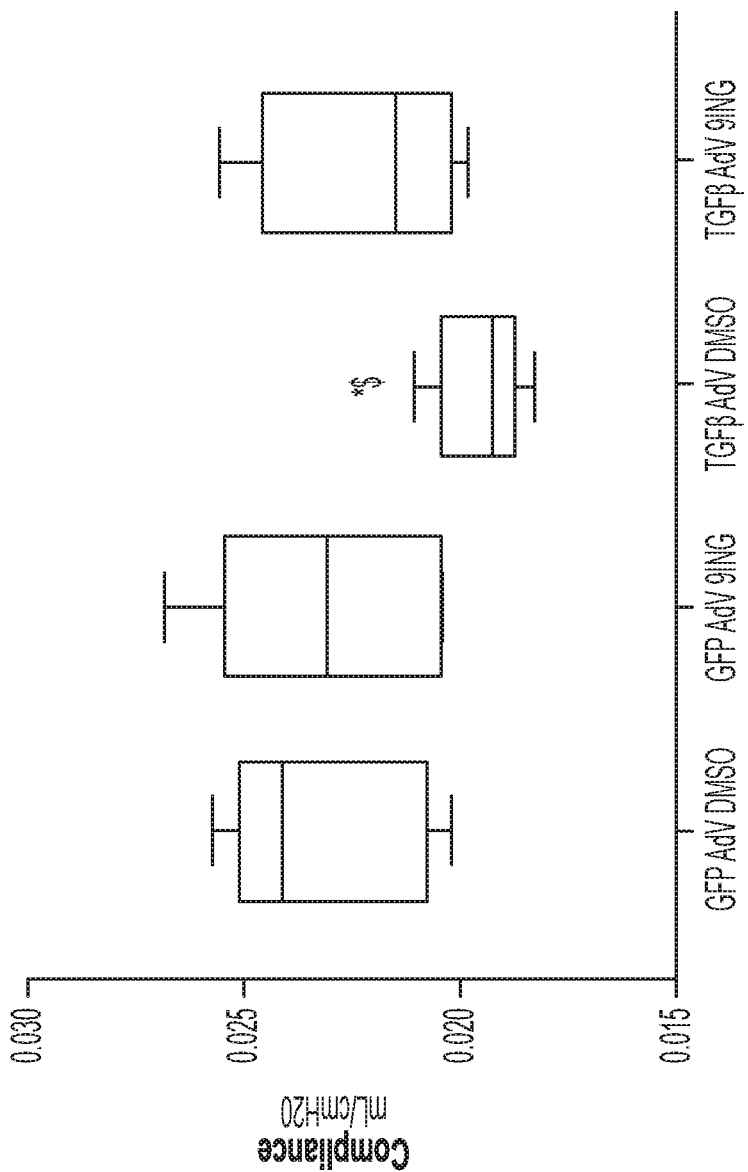
FIG. 3 is a graph showing lung compliance of mice intratracheally administered TGF-β adenovirus to induce pulmonary fibrosis. After 7 d, mice received daily intraperitoneal injections of 9-ING-41 (30 mg/kg) for the next 7 d. At the completion of the 14 d time course, lung compliance was determined. Data are expressed as a means±SEM. n=6 mice/condition. * indicates a p<0.05 statistical significance by the Mann-Whitney U test compared to control GFP-adenovirus and DMSO treatment. $ denotes p<0.05 compared to GFP adenovirus 9-ING-41 treatment.
Figure 4A:
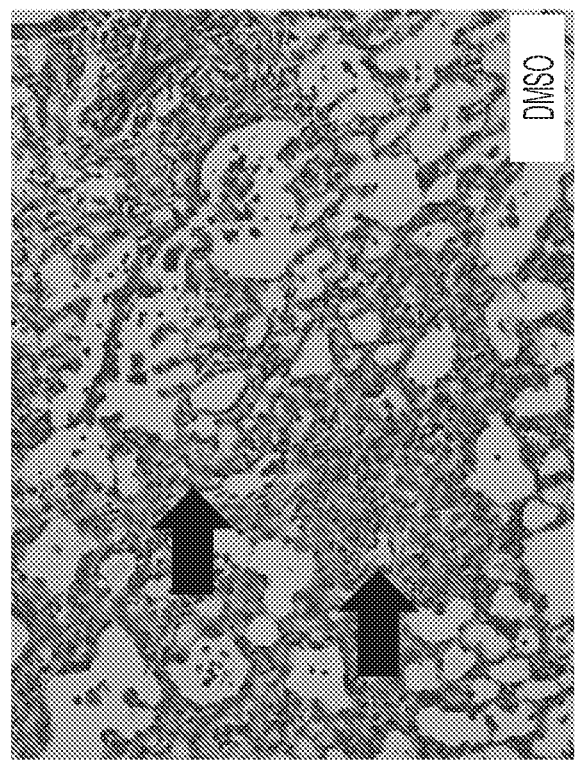
FIGS. 4A-4B show lung tissue sections from mice in which TGF-β adenovirus induced pulmonary fibrosis. Mice were treated with DMSO (FIG. 4A) or 9-ING-41 (FIG. 4B) (see Description of FIG. 3). Sections were Trichrome stained to show areas of injury and collagen. Solid arrows indicate areas of injury and increased collagen deposition. Images are representative of 30 fields/slide/condition. n=6 mice.
Figure 4B:
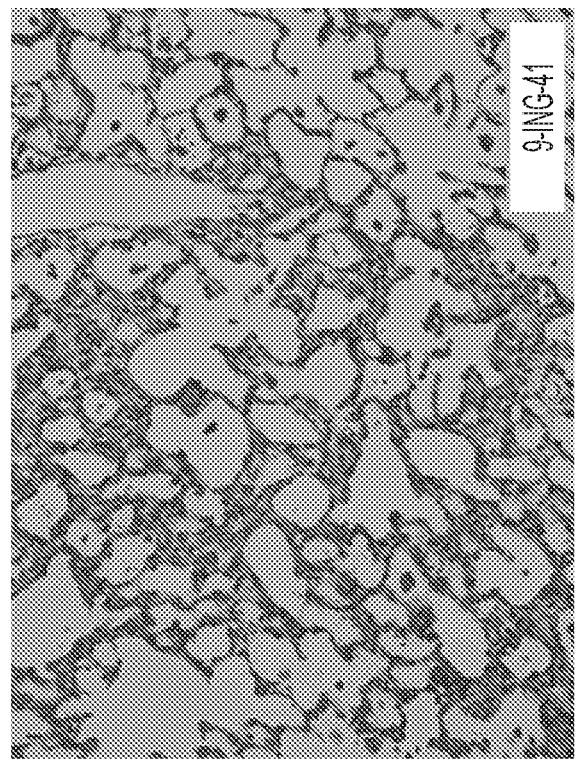
Figure 5A:
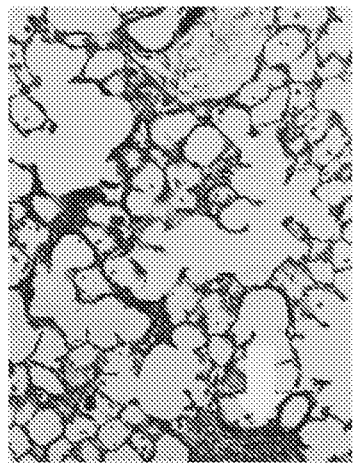
FIGS. 5A-5F show lung tissue sections (5 μm) from vehicle (FIG. 5A-5C) and -9-ING-41-treated (FIG. 5D-5F) mice. The sections were de-paraffinized and Trichrome stained to detect changes in lung architecture and collagen deposition (blue stain). Images were taken at 20× and represent 30 fields/slide/mouse, n=6 animals per treatment. Fibrotic foci are indicated by solid yellow arrows).
Figure 5B:
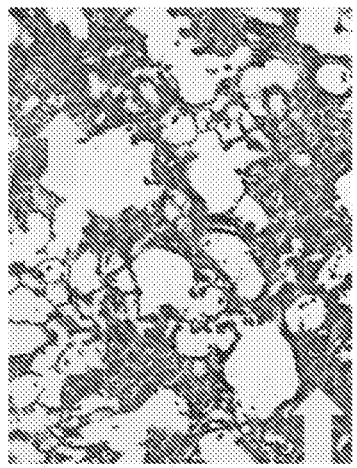
Figure 5C:
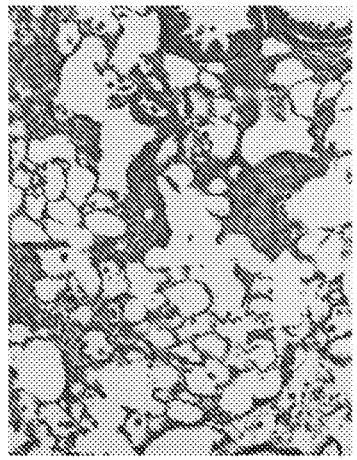
Figure 5D:
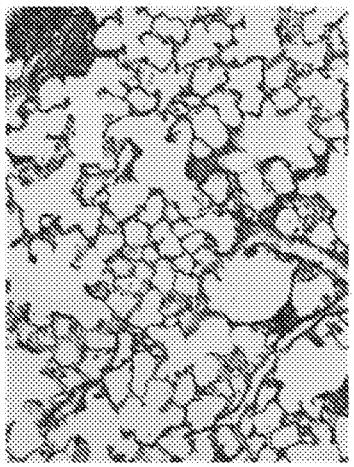
Figure 5E:
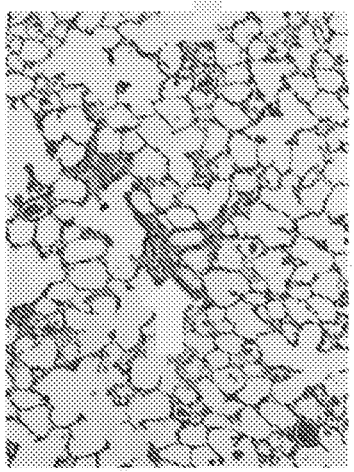
Figure 5F:
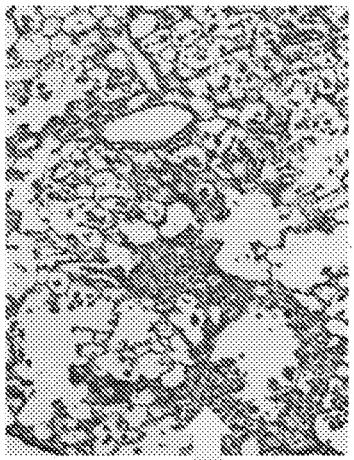

Results are shown in FIG. 3. 9-ING-41-treated mice demonstrated significantly improved lung compliance compared to various vehicle-treated or sham vector-treated controls. FIGS. 4A/4B show reduced areas of injury and increased collagen deposition in 9-ING-41-treated mice compared to DMSO-treated controls.

IPF is characterized by the increased presence of myofibroblasts and subsequent increased deposition of extracellular matrix (ECM) proteins such as collagen and fibronectin. In the present models of IPF, bleomycin sulfate and TGF-β adenovirus was introduced by intratracheal cannulation, a method that yields robust and consistent injury (thus requiring fewer animals to yield statistically significant results).

Bleomycin- and TGF-β-adenovirus-mediated fibrosis were characterized by the presence of fibrotic foci that contained collagen and other ECM matrix protein which contribute to lung scarring, loss of the normal lung architecture, and impaired lung function. Further, these fibrotic foci also contained increasing numbers of myofibroblasts, which are believed to be the primary source of increased ECM deposition.

To evaluate the efficacy of the preferred GSK-3β inhibitory compound, 9-ING-41 IPF, intervention was done at a time point at which alterations of pulmonary architecture and function were detectable. Based on preliminary studies, the 14 d time-point was selected for bleomycin injury studies and 7 d for TGF-β adenoviral studies. By completion of the time courses (28 d and 14 d respectively) 9-ING-41 treated mice in both models not only manifested improved lung function but also showed increased lung volume.

Based on the histopathological analyses discussed and exemplified above, the present inventors concluded that the reduced number of fibrotic foci in combination with reduced scarring contributed to restoration of lung function as a result of 9-ING-41 treatment. Confocal microscopic analyses further showed that the fibrotic foci found in 9-ING-41-treated mice were fewer in number, smaller and contained notably less collagen than in vehicle treated control animals. These similar findings in two independent models of pulmonary fibrosis show that 9-ING-41 treatment significantly improved IPF outcomes. Further, this effect was believed to result at least in part from attenuation of fibroblast-myofibroblast differentiation. The present results show that inhibition of GSK-3β with 9-ING-41 represents a novel therapy for IPF.

These are the first studies to demonstrate that the GSK-3β signaling pathway is critical for the induction of myofibroblast differentiation. These studies also show that the therapeutic targeting of GSK-3β attenuates the progression of pulmonary fibrosis; this effect is also expected to occur in human subjects. This work provides a basis for targeting the GSK-3β signaling pathway to control of fibroblast-myofibroblast differentiation and outcomes of pulmonary fibrosis as therapeutic targeting of GSK-3β mitigates fibrotic pulmonary remodeling in vivo. The significantly improved compliance and volumes produced by 9-ING-41 specifically are also important indices of its effectiveness in treating IPF in mouse models and is expected to occur in humans IPF patients as well.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

The present disclosure also encompasses the following aspects:

Aspect 1. An antifibrotic pharmaceutical composition formulated for injection or lung instillation comprising:
 (i) a benzofuran-3-yl-(indol3-yl) maleimide compound that inhibits enzyme glycogen synthase kinase 3, form β (GSK3β), which has at least at least 20% of the biological or biochemical activity of 9-ING-41 in an in vitro or in vivo assay.
 (ii) a pharmaceutically acceptable carrier or excipient.

Aspect 2. The pharmaceutical composition of aspect 1 wherein the compound is 9-ING-41, the chemical formula of which is:

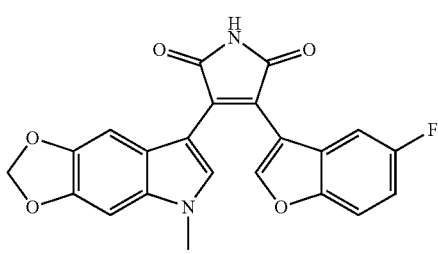 [SMILES: Cn1cc(C2=C(c3coc4ccc(F)cc34)C(=O)NC2=O)c2cc3c(cc21)OCO3]

or an analogue of 9-ING-41 which has at least 20% of the biological or biochemical activity of 9-ING-41 in an in vitro or in vivo assay.

Aspect 3. The pharmaceutical composition of aspect 2 wherein the compound is 9-ING-41.

Aspect 4. The pharmaceutical composition of any of aspects 1 to 3 formulated for lung instillation.

Aspect 5. A method for inhibiting proliferation and/or differentiation of lung myofibroblasts to fibrotic lung (FL) fibroblasts and reducing proliferation of said FL fibroblasts, comprising providing to said myofibroblasts and FL fibroblasts an effective GSK3β-inhibitory amount of the compound or composition of any of aspects 1-4.

Aspect 6. The method of aspect 5 wherein the compound is 9-ING-41 or said analogue thereof.

Aspect 7. The method of aspect 6 wherein the compound is 9-ING-41.

Aspect 8. The method of aspect 7 wherein the composition is formulated for lung instillation.

Aspect 9. The method of any of aspects 5 to 8 wherein said providing is in vivo.

Aspect 10. The method of aspect 9 wherein said providing is by lung instillation.

Aspect 11. The method of aspect 9 or 10 wherein said providing is to a human.

Aspect 12. A method for treating a mammalian subject having or developing a disease or condition characterized by idiopathic pulmonary fibrosis (IPF), comprising administering to the subject an effective amount of a pharmaceutical composition of any of aspects 1-4.

Aspect 13. The method of aspect 12 wherein said compound or composition comprises 9-ING-41 or said analogue thereof that has at least 20% of the biological or biochemical activity of 9-ING-41 in an in vitro or in vivo assay; Aspect 14. The method of aspect 13, wherein the compound is 9-ING-41.

Aspect 15. The method of any one of aspects 12 to 14 wherein the subject is a human.

Aspect 16. A use of the composition of any of aspects 1 to 4 for treating IPF in a mammalian subject, wherein said compound inhibits GSK3β and inhibits proliferation and/or differentiation of lung myofibroblasts to FL fibroblasts and reduces proliferation of said FL fibroblasts, and an effective amount of said composition is administered to a subject with IPF.

Aspect 17. The use according to aspect 16 wherein said compound is 9-ING-41 or said analogue thereof.

Aspect 18. The use according to aspect 17 wherein said compound is 9-ING-41.

Aspect 19. The use according to any of aspects 16-18 where said composition is administered by lung instillation.

Aspect 20. The use of a composition according to of aspects 1-4 for the manufacture of a medicament for treatment of IPF in a subject in need thereof, which compound inhibits GSK3β activity and inhibits proliferation and/or differentiation of lung myofibroblasts to FL fibroblasts and reduces proliferation of said FL fibroblasts.

Aspect 21. The use according to aspect 20 wherein said compound is 9-ING-41 or an analogue thereof that has at least 20% of the biological or biochemical activity of 9-ING-41 in an in vitro or in vivo assay.

Aspect 22. The use according to aspect 21 wherein said compound is 9-ING-41.

Aspect 23. The use according to any of aspects 20-22 for the manufacture of the medicament for lung instillation in the treatment of IPF.

Aspect 24. The use according to any of aspects 20-24 wherein the subject is a human.

What is claimed is:

1. A method of treating idiopathic pulmonary fibrosis (IPF) in a mammalian subject, comprising administering to the mammalian subject, an effective amount of a compound of Formula I Formula I

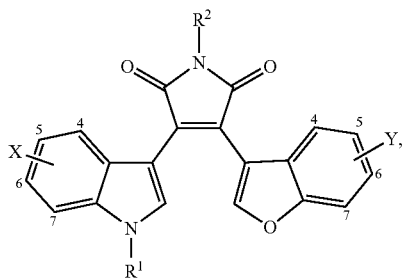

or a pharmaceutically acceptable salt or solvate thereof, wherein:
X is independently —H, halo, 5,6-methylenedioxy, —CN, —OMe, —OH, —OBn, —CF$_3$, —CH$_2$OH, —CH2OMe, —CH$_2$CH$_2$CO$_2$H, or —CH$_2$CH$_2$CO$_2$Et;
R$^1$ is —H, lower alkyl, lower alkyl substituted with a hydroxy, or lower alkyl substituted with —NH$_2$;
R$^2$ is —H, lower alkyl, lower alkyl substituted with a hydroxy, or lower alkyl substituted with —NH$_2$; and
Y is independently —H, halo, —OMe, —OH, —OBn, —CF$_3$, —CH$_2$OH, —CH$_2$OMe, —NO$_2$, —CN, or —C═CH$_2$.

2. A method of treating idiopathic pulmonary fibrosis (IPF) in a mammalian subject, comprising administering to the mammalian subject, a pharmaceutical composition comprising:
(i) an effective amount of a compound of Formula I Formula I

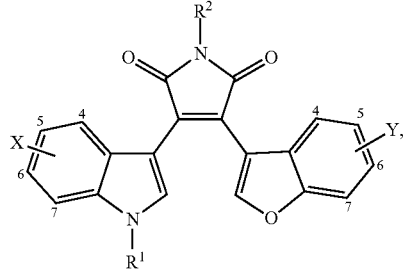

or a pharmaceutically acceptable salt or solvate thereof, wherein:

X is independently —H, halo, 5,6-methylenedioxy, —CN, —OMe, —OH, —OBn, —CF$_3$, —CH$_2$OH, —CH2OMe, —CH$_2$CH$_2$CO$_2$H, or —CH$_2$CH$_2$CO$_2$Et;

R$^1$ is —H, lower alkyl, lower alkyl substituted with a hydroxy, or lower alkyl substituted with —NH$_2$;

R$^2$ is —H, lower alkyl, lower alkyl substituted with a hydroxy, or lower alkyl substituted with —NH$_2$; and Y is independently —H, halo, —OMe, —OH, —OBn, —CF$_3$, —CH$_2$OH, —CHOMe, —NO$_2$, —CN, or —C≡CH$_2$; and (ii) a pharmaceutically acceptable carrier or excipient.

3. The method of claim 1, wherein the compound of Formula I is 9-ING-41:

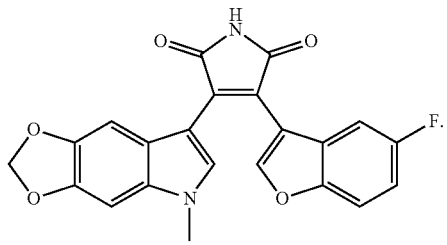

9-ING-41

4. The method of claim 1, wherein said mammalian subject is a human.

5. The method of claim 1, wherein said administering is by inhalation.

6. The method of claim 2, wherein the compound of Formula I is 9-ING-41:

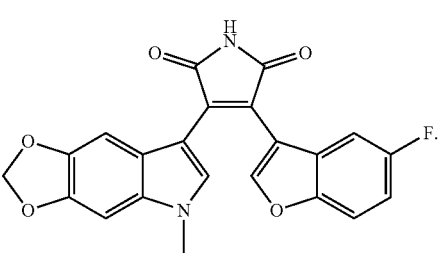

9-ING-41

7. The method of claim 2, wherein said mammalian subject is a human.

8. The method of claim 2, wherein said administering is by inhalation.

* * * * *